United States Patent

Seshimoto et al.

[11] Patent Number: 4,578,173
[45] Date of Patent: Mar. 25, 1986

[54] ION SELECTIVE ELECTRODE AND METHOD OF MAKING ION SELECTIVE ELECTRODES

[75] Inventors: Osamu Seshimoto; Mitsuharu Nirasawa, both of Asaka, Japan

[73] Assignee: Fuji Photo Film Co., Ltd., Kanagawa, Japan

[21] Appl. No.: 732,368

[22] Filed: May 9, 1985

[30] Foreign Application Priority Data

May 10, 1984 [JP] Japan ................................. 59-93774
Jun. 20, 1984 [JP] Japan ................................ 59-128239

[51] Int. Cl.$^4$ ............................................ G01N 27/30
[52] U.S. Cl. .................................... 204/416; 204/418; 204/419; 204/435; 427/123; 427/125; 427/126.1; 427/126.5
[58] Field of Search ............... 204/416, 418, 419, 420, 204/1 A, 435; 427/123, 125, 126.1, 126.5

[56] References Cited

U.S. PATENT DOCUMENTS 3,856,649 12/1974 Genshaw .......................... 204/418
4,053,381 10/1977 Hamblen et al. ............... 204/418 X Primary Examiner—G. L. Kaplan
Attorney, Agent, or Firm—Toren, McGeady, Stanger, Goldberg & Kiel

[57] ABSTRACT

An integral ion selective electrode for the analysis of a potassium ion comprising a support, an electroconductive metal layer such as a silver metal layer, a layer of a water-insoluble salt of said metal such as a silver chloride layer, an electrolyte layer which comprises an electrolyte salt of a potassium ion with the same anion as the anion of the water-insoluble salt, said electrolyte layer being substantially free from a binder, and an ion selective layer, which is characterized in that the electrolyte layer comprises crystalline electrolyte having a mean crystal size of not more than 60 μm. Processes preferably employable for the preparation of the ion selective electrode are also disclosed.

10 Claims, 3 Drawing Figures

ION SELECTIVE ELECTRODE AND METHOD OF MAKING ION SELECTIVE ELECTRODES

BACKGROUND OF THE INVENTION

1. Field of the Invention

The present invention relates to an ion selective electrode and processes for the preparation of the same. More particularly, the invention relates to an ion selective electrode appropriately employable for the potentiometric determination of a potassium ion, and processes for the preparation of the electrode.

2. Description of Prior Arts

The ion selective electrode is a device for the potentiometric determination of ion concentration in an aqueous sample, and a body fluid such as blood or serum. Its elemental structure is disclosed, for instance, in Japanese Patent Provisional Publication No. 52(1977)-142584 and U.S. Pat. No. 4,053,381. In more detail, the ion selective electrode has an integral structure comprising a support, an electroconductive metal layer (e.g., deposited silver metal layer), a layer of a water-insoluble salt of said metal (e.g., a layer of silver chloride), an electrolyte layer which comprises an electrolyte salt of a cation (e.g., potassium ion or sodium ion) with the same anion as the anion of the water-insoluble salt, for instance, potassium chloride or sodium chloride.

In practically determining ion concentration by means of an ion selective electrode (i.e., half cell) having the above-described elemental structure, the following procedures are adopted: A couple of ion selective electrodes A & B are connected via a water-retainable bridge. On the ion selective electrodes A & B are spotted a standard liquid (reference liquid) and a liquid sample, respectively, and the potential difference between both electroconductive layers of the ion selective electrodes A & B are measured after lapse of a certain period of time. The measured potential difference is then compared against a calibration curve to determine the concentration of the electrolyte. Alternatively, a couple of ion selective electrodes insulated from each other by a scratched groove disclosed in Japanese Patent Provisional Publication No. 58(1983)-156848 can be used for the measurement in the same manner.

The ion selective electrode is composed basically of the above-stated simple structure and can be manufactured in the form of a small sized chip. Accordingly, the ion selective electrode is very advantageously employed for the determination of an electrolyte in a small amount of a liquid sample such as a body liquid. In most cases, a body liquid is available for the determination in a very limited amount. Moreover, the ion selective electrode is employable as a disposable device, because it can be formed in a simple structure and in a small size.

It has been noted, however, that a measured value obtained in the use of a small sized ion selective electrode sometimes is not reliable. This arises from fluctuation of electric potential (i.e., potential drift) which often takes place in the measurement procedure. It is thought that the potential drift is reduced by the use of an ion selective electrode in which the thickness of each of the functional layers is increased. However, the increase of the thickness of layers not only results in increase of cost for manufacturing the device, but also results in decrease of the sensitivity.

An improvement for obviating the occurrence of the potential drift or other disadvantageous problems has been proposed in Japanese Patent Provisional Publication No. 57(1982)-17852. This improvement comprises preparing a binderless electrolyte layer by vapor deposition of the electrolyte or by a series of procedures of coating an aqueous electrolyte solution containing no binder and then drying the coated layer. This art provides an ion selective electrode which is reduced in occurrence of the potential drift taken place in the conventional ion selective electrode. Nevertheless, more reduction of the possible potential drift is desired for the purpose of enhancing the accuracy of the meaurement in the use of ion selective electrode.

SUMMARY OF THE INVENTION

According to the study of the present inventors, it has been noted that the electrolyte layer prepared from an aqueous electrolyte solution containing no binder by a coating-drying procedure comprises a relatively large sized crystalline electrolytes. Therefore, the crystalline elecrolytes are not distributed uniformly in the layer and the resulting electrolyte layer is apt to have a large thickness. The non-uniform electrolyte layer and thick electrolyte layer both serve to decrease the accuracy of measurement.

The preparation of an electrolyte layer by vapor deposition of an electrolyte is disadvantageous in an industrially available scale, because the vapor deposition of an electrolyte giving a low vapor pressure is difficultly employed, and otherwise the vapor deposition of an electrolyte decomposable at a vaporized temperature requires specific carefulness so that no high vaporization efficiency is expected.

Accordingly, a primary object of the present invention is to provide an ion selective electrode which is appropriately employable for the analysis of a potassium ion through potentiometric determination and is reduced in the occurrence of phenomena bringing about measurement errors such as the potential drift.

Another object of the invention is to provide an ion selective electrode for the determination of a potassium ion which is shortened in the response period at the measurement.

A further object of the invention is to provide an ion selective electrode appropriately employable for the analysis of a potassium ion a body liquid.

A still further object of the invention is to provide a process appropriately employable for the preparation of an ion selective electrode for the analysis of a potassium ion through potentiometric determination and is reduced in the occurrence of phenomena bringing about measurement errors such as potential drift.

The present invention resides in a integral ion selective electrode for the analysis of a potassium ion comprising a support, an electroconductive metal layer, a layer of a water-insoluble salt of said metal, an electrolyte layer which comprises an electrolyte salt of a potassium ion with the same anion as the anion of the water-insoluble salt, said electrolyte layer being substantially free from a binder, and an ion selective layer, which is characterized in that the electrolyte layer comprises crystalline electrolyte having mean size of not more than 60 μm.

The above-described ion selective electrode can be prepared by a process which comprises forming the electrolyte layer by coating an aqueous solution containing the electrolyte salt but containing substantially no binder on the layer of a water-insoluble salt and drying the thus coated layer by bringing it in contact with a stream of gas maintained at a temperature of not lower than 40° C.

Further, the above-described ion selective electrode can be prepared by a process which comprises forming the electrolyte layer by coating a solution containing the electrolyte salt but containing substantially no binder in a mixture of water and an organic solvent on the layer of a water-insoluble salt and drying thus coated layer.

DETAILED DESCRIPTION OF THE INVENTION

Figure 1:
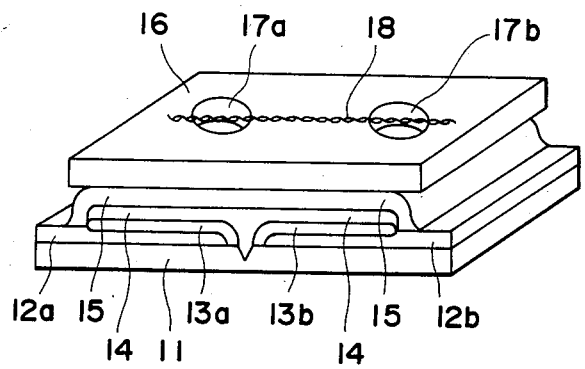
FIG. 1 illustrates an ion selective electrode equipped with a bridge which is employed for the measurement according to the differential method.

As described hereinbefore, the elemental structure of the ion selective electrode provided by the present invention which comprises a support, an electroconductive metal layer, a layer of a water-insoluble salt of said metal, an electrolyte layer comprising an electrolyte salt of a potassium ion with the same anion as the anion of the water-insoluble salt, said electrolyte layer being substantially free from a binder, and an ion selective layer is as such known. For instance, such embodiment is disclosed in Japanese Patent Provisional Publication No. 57(1982)-17852. The ion selective electrode of the invention can be prepared in the same manner as in the conventional art except that the electrolyte layer is prepared in a different manner. The constitution of the ion selective electrode and materials employed for the preparation can be determined on the basis of the disclosures in Japanese Patent Provisional Publications Nos. 52(1977)-142584, 57(1982)-17852 and 58(1983)-211648.

For instance, the support can be prepared from a film or sheet of plastic material such as polyethylene terephthalate. A representative electroconductive metal layer is a silver metal layer formed on a surface of the support by vapor deposition. In the case that the electroconductive metal layer is a silver metal layer, the layer of a water-insoluble salt can be produced by chemical oxidation-chlorination of the surface portion of the silver metal layer to form a silver chloride layer, or by coating a dispersion containing silver chloride and a binder on the surface of the silver metal layer and drying the coated layer.

On the layer of a water-insoluble salt is formed an electrolyte layer. The constitution of the electrolyte layer is a characteristic feature of the invention and shall be described hereinafter in detail.

The ion selective layer is capable of selecting a specific ion, and shows a high electric resistance and is a substantially electric insulative in a dry state prior to contact with a liquid sample or a reference liquid. The capability of selecting a specific ion includes not only a property of selectively allowing permeation of the specific ion or selectively responding to the specific ion but also a property of selecting a specific ion from other ions or substances with a time differential enough for detecting the specific ion. Moreover, certain materials employable for the formation of the ion selective layer are capable of detecting a potential difference on the ion activity change occurring in the course of ion exchange, whereby showing the same property as the property of selecting a specific ion. This property is also included in the capacity of selecting a specific ion.

The ion selective layer ought to be water-insoluble, because a liquid sample and a reference sample both are aqueous liquids. The ion selective layer can be either hydrophylic or hydrophobic, as far as the layer is water-insoluble. However, a hydrophobic ion selective layer is preferred.

The ion selective layer can be prepared in the known manner. For instance, a solution of an ion carrier and a hydrophobic organic binder in an ion-carrier solvent is coated on the electrolyte layer and dried to give an ion selective layer. The ion carrier is generally coated in the amount of 0.05–10 g/m$^2$, and the thickness of the ion selective layer ranges from approx. 3 μm to approx. 125 μm, preferably from approx. 5 μm to approx. 50 μm. Examples of the ion carrier include valinomycin, cyclic polyethers, tetralactones, macrolide actins, enniatin, potassium tetraphenyl borate and their derivatives. Examples of the ion carrier solvent include phthalates, sebacates, aromatic or aliphatic ethers and adipates. Concrete examples of the solvent are described in Japanese Patent Publication No. 58(1983)-4981. For instance, there can be mentioned bromophenyl phenyl ether, 3-methoxyphenyl phenyl ether, 4-methoxyphenyl phenyl ether, dimethyl phthalate, dibutyl phthalate, didodecyl phthalate, dioctylphenyl phosphate, dicresyl phosphate-bis(2-ethylhexyl)phthalate, octyldiphenyl phosphate, tritolyl phosphate, dioctyl adipate and dibutyl sebacate. Moreover, a great number of utilizable solvents are known.

The hydrophobic organic binder can be a film-forminng natural polymer, its derivative, or a synthetic polymer. Examples of the hydrophobic organic binder include cellulose ester, polyvinyl chloride, vinyl chloride-vinyl acetate copolymer, polyvinylidene chloride, polyacrylonitrile, polyurethane, and polycarbonate of bisphenol A.

Details on the ion carrier, ion carrier solvent, hydrophobic organic binder and ion selective layer are given not only in the aforementioned Japanese Patent Publication No. 58(1983)-4981, but also in Japanese Patent Provisional Publication No. 58(1983)-156848, U.S. Pat. Nos. 4,053,381, 4,171,246, and 4,214,968, and Research Disclosure No. 16113 (September 1977).

Moreover, an ion exchange material can be used for the formation of the ion selective layer. In this case, a response on the potential difference originating from change of ion activity caused by the ion exchange is measured. Appropriate ion exchange materials and preparation of the ion selective layer using these materials are described in Japanese Patent Publication 52(1977)-47717. A representative example of the ion exchange material is trialkylammonium chloride for ion exchange of a chloride ion.

The ion selective electrode of the present invention is characterized in that the potassium salt electrolyte layer is substantially free from a binder and comprises crystalline electrolytes having means size of not more than 60 μm, preferably 0.1 to 50 μm, more preferably 0.5 to 40 μm, in which the crystalline electrolyte is preferably distributed densely and uniformly on the layer of a water-insoluble salt of a metal constituting the electroconductive layer (hereinafter referred to as "water-insoluble salt layer).

Preferably, the crystalline electrolytes (electrolyte crystals) are not arranged in piles in the direction vertical to the plane of the ion selective electrode. Accordingly, the mean thickness of the electrolyte layer preferably is almost equal to the mean size of the crystalline electrolytes.

In the ion selective electrode of the present invention, the electrolyte layer is formed by arranging uniformly crystalline electrolyte of a small size without using a binder over the surface of the water-insoluble salt layer. The crystalline electrolyte is densely arranged, and a relatively thin electrolyte layer can be formed. An ion selective layer having such electrolyte layer shows quick response and is prominently reduced in occurrence of the potential drift. Moreover, the ion selective electrode of the invention is almost free from separation of the functional layers at the electrolyte layer which is sometimes observed in the use of an ion selective electrode having a binderless electrolyte layer. The reason is thought to reside not only in evenness of the electrolyte layer and decrease of the thickness but also in that the small sized electrolyte crystals defined in the invention are at least partly engaged physically with the water-insoluble salt layer. Particularly, where the water-insoluble salt layer is a porous silver chloride layer, the engagement between the crystalline electrolyte and the water-insoluble salt layer (i.e., silver chloride layer) is prominently observed.

In the case that the electrolyte layer is nearly a single particle layer composed of regulaly distributed small-sized crystalline particles, the electrolyte layer is substantially free from poor contact or adhesion between the electrolyte layer and the ion selective layer, which are sometimes observed in the binder-containing electrolyte layer of the conventional ion selective electrode.

According to the study of the present inventors, the potassium electrolyte salt crystals having the small mean size defined in the invention are not formed by the conventional method which comprises procedures of simply coating an aqueous binderless electrolyte solution on the surface of the water-insoluble salt layer and drying under ambient conditions.

It has been discovered that the conventional process comprising procedures of coating an aqueous solution of potassium electrolyte salt such as potassium chloride or potassium bromide on the water-insoluble salt layer and allowing the coated layer to dry at room temperature gives crystalline electrolyte of large mean size such as not less than 70 $\mu$m, generally 70–100 $\mu$m. The electrolyte layer composed of such large sized crystalline electrolyte is poor in the evenness of the distribution of the electrolytes and the thickness of the electrolyte layer. Accordingly, the potential drift is apt to appear more easily and the response time becomes longer because of thus formed thick electrolyte layers.

The electrolyte layer of the present invention can be prepared by a process which comprises forming the electrolyte layer by coating an aqueous solution of the electrolyte salt on the water-insoluble salt layer and drying thus coated layer by bringing it in contact with a stream of gas maintained at a temperature of not lower than 40° C. (preferably 50°–200° C.), whereby producing a layer of of crystalline electrolyte having mean size of not more than 60 $\mu$m (preferably 0.1–40 $\mu$m) over the water-insoluble salt layer.

Preferably, the electrolyte layer of the invention is prepared by a process which comprises forming the electrolyte layer by coating a solution of the electrolyte salt in a mixture of water and an organic solvent on the water-insoluble salt layer and drying thus coated layer. There is no specific limitation on the drying conditions, but the coated layer is preferably dried by a stream of gas at a temperature of not lower than 40° C. More preferably, a temperature of a stream of gas ranges from 50° to 200° C.

The latter process using a mixture of water and an organic solvent is particularly preferred to produce a crystalline electrolyte of a smaller size. Moreover, this process is advantageous in the preparation of the ion selective electrode in a continuous form. In more detail, the ion selective electrode is manufactured industrially by initially producing an ion selective electrode in a continuous form on a continuous plastic sheet and then dividing it to give a multiple of ion selective electrodes. The use of a mixture of water and an organic solvent (which is miscible with water) is effective not only to shorten the period required for the formation of the electrolyte layer but also to facilitate the preparation of the electrolyte layer comprising crystalline electrolytes uniformly and densely distributed over the water-insoluble salt layer. The mixture of water and an organic solvent is preferably in the range of 2:8 to 8:2.

Examples of the organic solvent include lower aliphatic alcohols such as methanol, ethanol, propanol and isopropanol, aliphatic ketones such as acetone, methyl ethyl ketone and diethyl ketone, ethers such as diethyl ether and tetrahydrofuran, and esters of lower aliphatic acids with lower aliphatic alcohols such as ethyl acetate and butyl acetate. The organic solvent can be employed singly and in combination.

There is no specific limitation on the concentration of the aqueous electrolyte solution (which may contain an organic solvent) employed for the preparation of the electrolyte layer. Generally, the concentration of the electrolyte in the solution ranges from approx. 0.5 to approx. 20% by weight, preferably approx. 0.5 to approx. 15% by weight, more preferably approx. 0.5 to approx. 10% by weight. An electrolyte solution of a higher concentration within the above-defined range is preferably employed for enhancing the efficiency in the industrial manufacturing of the electrode.

The anion which is a counter ion to the potassium ion, both consisting in the electrolyte salt of the electrolyte layer of the invention ought to be identical to the anion of the water-insoluble salt. Accordingly, the anion is selected in consideration of the whole constitutional conditions of the ion selective electrode. Generally, the electroconductive layer is made of a silver metal, and the water-insoluble salt is composed of silver chloride. For this reason, potassium chloride is generally employed as the electrolyte. Nevertheless, if the anion of the water-insoluble salt is an anion other than the chloride ion, such as a bromide ion, iodine ion, sulfonium ion or carboxylic ion, the anion of the electrolyte salt is selected to be consistent with the above-selected anion.

The present invention is further described by the following examples.

EXAMPLE 1

On a polyethylene terephthalate film (thickness: 188 $\mu$m, 30 mm × 100 mm) was formed a silver metal layer of approx. 800 nm thick by vapor deposition under vacuum. The deposited silver metal layer is covered at both sides by means of a liquid resist of the polymer composition described in Japanese Patent Provisional Publication No. 58(1983)-102146. The center portion of the deposited silver metal layer was removed by scratching with a cutter knife to form an insulating area of a V shape.

The exposed portion of the deposited silver metal layer was processed in a processing solution containing hydrochloric acid and potassium dichromate (aqueous solution containing hydrochloric acid 36 mmol./l and potassium dichromate 16 mmol./l) for approx. 60 sec., whereby the oxidation and chlorination took place. After the processing was complete, the composite element was washed with water and dried to give a filmy silver-silver chloride electrode (i.e., a composite of the support, electroconductive silver metal layer, and a silver chloride layer).

On the silver-silver chloride electrode film was coated an aqueous potassium chloride (3%) solution, and the coated layer was dried by applying thereto an air stream of approx. 150° C. for approx. 3 min. The weight of the electrolyte layer was 1.0 g/m² upon dryness. Microscopic observation indicated that the dried electrolyte layer was composed of a great number of potassium chloride fine crystals having a mean size of approx. 30 μm which were densely and uniformly distributed over the silver chloride layer.

On the thus formed electrolyte layer was then coated a potassium ion selective layer (thickness 20 μm) of the below-described composition formed in the conventional manner.

| Composition of potassium ion selective layer | |
| --- | --- |
| VYNS* | 0.9 g. |
| Dioctyl adipate | 1.2 g. |
| Valinomycin | 44 mg. |
| Potassium tetrakis-p-chlorophenyl borate | 18 mg. |
| Methyl ethyl ketone | 5 g. |
| 1% SH-510 (polysiloxane, methyl ethyl ketone solution) | 0.05 g. |

(Remark) VYNS: vinyl chloride-vinyl acetate copolymer available from Union Carbide Corp.

Thus, Ion Selective Electrode I for the analysis of potassium ion was prepared.

COMPARISON EXAMPLE 1

On a silver-silver chloride electrode film prepared in the same manner as in Example 1 was coated an aqueous potassium chloride (3%) solution. The coated layer was then allowed to stand at room temperature (approx. 20° C.) for approx. 5 hours to dryness. Thus, a dry electrolyte layer of 1.0 g/m² was formed. The microscopic observation indicated that the dried electrolyte layer was composed of a great number of potassium chloride crystals having a mean size of approx. 80 μm which were distributed over the silver chloride layer.

On the thus formed electrolyte layer was then coated a potassium ion selective layer in the same manner as in Example 1 to prepare Ion Selective Electrode II for the analysis of potassium ion.

Evaluation of Ion Selective Electrode

A liquid receiver of a plastic film provided with a couple of liquid receiving openings was fixed onto the surface of the ion selective electrode under adhesion. The two liquid receiving openings are connected to each other with a polyester spun thread bridge. Thus, an electrode device for the analysis of potassium ion was prepared. The electrode device for the potassium ion analysis is schematically illustrated in FIG. 1. In FIG. 1, 11 indicates the polyethylene terephthalate film (support), each of 12a and 12b indicates the deposited silver metal layer (the deposited silver metal layer is divided by the scratched groove to expose the surface of the support, thereby giving two separated areas), each of 13a and 13b indicates the silver chloride layer, 14 indicates the potassium chloride (electrolyte) layer, 15 indicates the ion selective layer, 16 indicates the liquid receiver, each of 17a and 17b indicates the liquid receiving opening, and 18 indicates the bridge.

In one liquid receiving opening 17a was spotted a potassium ion-containing reference solution (Calibrate 2,) and in another liquid receiving opening 17b was spotted a liquid sample (Calibrate 1, 2 or 3 was employed). In the measurement according to a differential method, the within-run precision was measured in the conventional manner. The results are set forth in Table 1.

TABLE 1

| | CV (%) | | K concentration (meq/l) | |
| --- | --- | --- | --- | --- |
| | Elec. I | Elec. II | Nominal | Observed |
| Calibrate 1 | 2.0 | 3.2 | 2.8 | 2.9 |
| 2 | 2.5 | 3.5 | 4.9 | 4.9 |
| 3 | 2.8 | 3.0 | 7.9 | 7.8 |

Remark: The slope value of Calibrate 1 was 63 mV/decade.

In the above-described measurements, the Electrode I prepared in Example 1 showed no value deviating from the expected value (±50 mV) even in fifty times-repeated runs, while the Electrode II prepared in Comparison Example 1 showed values deviating from the expected value (±50 mV) in a ratio of 8 times per fifty times-repeated runs.

EXAMPLE 2

The procedure of Example 1 was repeated except that the thickness of the ion selective layer was changed from 20 μm to 25 μm to prepare an ion selective electrode for the analysis of potassium ion (Ion Selective Electrode III).

The above-described evaluation was performed on the Ion Selective Electrode III. The results are almost the same as those given on the Ion Selective Electrode I.

EXAMPLE 3

On a silver-silver chloride electrode film prepared in the same manner as in Example 1 was coated an aqueous potassium chloride (3%) solution. The coated layer was then dried by applying an air stream (80° C.) for 3 min at a rate of 2.5 m/sec. Thus, a dry electrolyte layer of 1.3 g/m² was formed. The microscopic observation indicated that the dried electrolyte layer was composed of a great number of fine potassium chloride crystals having a mean size of approx. 35 μm which were uniformly and densely distributed over the silver chloride layer.

On the thus formed electrolyte layer was then coated a potassium ion selective layer in the same manner as in Example 1 to prepare Ion Selective Electrode IV for the analysis of potassium ion.

On the Ion Selective Electrode IV was performed the evaluation according to the differential method in the same manner as on the Ion Selective Electrodes I and II. The results are set forth in Table 2.

TABLE 2

|  | CV (%) | K concentration (meg/l) | |
| --- | --- | --- | --- |
|  | Elec. IV | Nominal | Observed |
| Hiland Q-II | 2.8 | 6.3 | 6.2 |
| Hiland Q-I | 2.3 | 4.5 | 4.5 |
| Omega-C | 2.7 | 2.6 | 2.6 |

In the above-described measurements, the Electrode IV showed no value deviating from the expected value even in fifty times-repeated runs.

EXAMPLE 4

A filmy silver-silver chloride electrode (reference electrode) and the Ion Selective Electrode I for the potassium ion analysis prepared in Example 1 were connected to each other by means of a combination of a liquid receiver and a bridge in the same manner as illustrared in FIG. 1.

On the reference electrode was spotted a reference liquid (Calibrate 2), while on the Ion Selective Electrode I was spotted a liquid sample (Calibrate 1, 2 or 3). The variation with time of the potential was measured according to the known direct method. The results are illustrated in FIG. 2.

Figure 2:
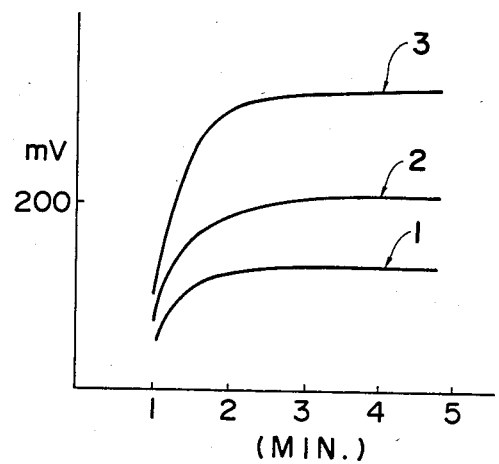
FIG. 2 shows graphically a variation with time of elecric potential observed in the measurement according to the direct method using an ion selective electrode of the invention.

As is clear from FIG. 2, the potential reached a stable value within a very short time.

EXAMPLE 5

The measurement by the same direct method as in Example 4 was repeated on the Ion Selective Electrode I for the potassium ion analysis using a liquid sample containing potassium chloride in the amount of 0.5%, 1.0%, 2.0%, 3.0%, 4.0%, 5.0%, or 10.0%. The measured values all were within approx. −230 mV.

The similar measurement was performed according to the differential method to give a CV=2.0–3.5%.

EXAMPLE 6

On a silver-silver chloride electrode film prepared in the same manner as in Example 1 was coated a potassium chloride solution containing 6 g. of potassium chloride in a mixture of ethanol (35 g.), acetone (50 g.) and water (110 g.). The coated layer was then allowed to stand at room temperature to dryness. Thus, a dry electrolyte layer of 2.5 g/m$^2$ was formed. The microscopic observation indicated that the dried electrolyte layer was composed of a great number of fine potassium chloride crystals having a mean size of approx. 55 μm which were uniformly and densely distributed over the silver chloride layer.

On the thus formed electrolyte layer was then coated a potassium ion selective layer in the same manner as in Example 1 to prepare Ion Selective Electrode V for the analysis of potassium ion.

EXAMPLE 7

The procedures of Example 6 were repeated except that a continuous polyethylene terephthalate (PET) film (length 1000 mm) was employed, the coating of the electrolyte solution was performed by means of a continuous coater, and the drying was performed by applying to the coated layer a stream of warm air at 60° C. for approx. 2 min. at a rate of 2.5 m/sec. Thus, a dry electrolyte layer of 2.5 g/m$^2$ was formed. The microscopic observation indicated that the dried electrolyte layer was composed of a great number of fine potassium chloride crystals having a mean size of approx. 35 μm which were uniformly and densely distributed over the silver chloride layer not only in the width direction but also in the longitudinal direction.

On the thus formed electrolyte layer was then coated a potassium ion selective layer in the same manner as in Example 1 to prepare Ion Selective Electrode VI for the analysis of potassium ion.

Evaluation of Ion Selective Electrode

The Ion Selective Electrodes V and VI were evaluated in the same manner as described hereinbefore. The results are set forth in Table 3.

TABLE 3

|  | CV (%) | | K concentration (meq/l) | |
| --- | --- | --- | --- | --- |
|  | Elec. V | Elec. VI | Nominal | Observed |
| Calibrate 1 | 2.0 | 1.0 | 2.8 | 2.9 |
| 2 | 2.5 | 1.5 | 4.9 | 4.9 |
| 3 | 2.1 | 1.2 | 7.9 | 7.9 |

In the above-described measurement, the Electrodes V and VI both showed no value deviating from the expected value (±50 mV) even in fifty times-repeated runs.

Potential Measurement According to Direct Method

The Ion Selective Electrodes V and VI were further evaluated according to the direct method described in Example 4. The results are illustrated in FIG. 3.

Figure 3:
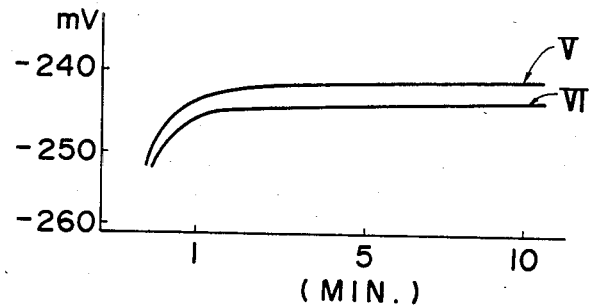
FIG. 3 shows graphically a variation with time of elecric potential observed in the measurement according to the direct method using another ion selective electrode of the invention.

As is apparent from FIG. 3, the potential reached a stable value within a very short time in both cases.

EXAMPLE 8

The procedures of Example 6 were repeated except that the ion selective layer was prepared by the use of the following composition:

| Composition of potassium ion selective layer | |
| --- | --- |
| VYNS | 0.9 g. |
| Dioctyl adipate | 1.2 g. |
| Valinomycin | 44 mg. |
| Methyl ethyl ketone | 5 g. |
| 1% SH-510 (polysiloxane, methyl ethyl ketone solution) | 0.05 g. |

The above-described evaluation was performed on the resulting ion selective electrode. The results are almost the same as those given on the Ion Selective Electrode V.

We claim:

1. An integral ion selective electrode for analysis of a potassium ion comprising in order a support, an electroconductive metal layer, a layer of a water-insoluble salt of said metal, an electrolyte layer which comprises an electrolyte salt of a potassium ion with the same anion as the anion of the water-insoluble salt, said electrolyte layer being substantially free from a binder, and an ion selective layer, which is characterized in that the electrolyte layer comprises crystalline electrolyte having a mean crystal size of not more than 60 μm.

2. The ion selective electrode as claimed in claim 1, wherein the mean crystal size of the crystalline electrolyte ranges from 0.1 to 50 μm.

3. The ion selective electrode as claimed in claim 1, wherein the mean thickness of the electrolyte layer is substantially equal to the mean size of the crystalline electrolyte.

4. The ion selective electrode as claimed in any one of claims 1 to 3, wherein said electrolyte salt is potassium chloride.

5. The ion selective electrode as claimed in any one of claims 1 to 3, wherein said layer of a water-insoluble salt is of silver chloride and said electrolyte salt is potassium chloride.

6. A process for the preparation of an integral ion selective electrode for analysis of a potassium ion comprising in order a support, an electroconductive metal layer, a layer of a water-insoluble salt of said metal, an electrolyte layer which comprises an electrolyte salt of a potassium ion with the same anion as the anion of the water-insoluble salt, and electrolyte layer being substantially free from a binder, and an ion selective layer, which is characterized in that the electrolyte layer is formed by coating an aqueous solution of said electrolyte salt on the layer of a water-insoluble salt and drying thus coated layer by bringing it in contact with a stream of gas maintained at a temperature of not lower than 40° C., thereby producing a layer of of crystalline electrolyte having a mean crystal size of not more than 60 μm over the layer of a water-insoluble salt.

7. A process for the preparation of an integral ion selective electrode for analysis of a potassium ion comprising in order a support, an electroconductive metal layer, a layer of a water-insoluble salt of said metal, an electrolyte layer which comprises an electrolyte salt of a potassium ion with the same anion as the anion of the water-insoluble salt, said electrolyte layer being substantially free from a binder, and an ion selective layer, which is characterized in that the electrolyte layer is formed by coating a solution of said electrolyte salt in a mixture of water and an organic solvent on the layer of a water-insoluble salt and drying thus coated layer, thereby producing a layer of of crystalline electrolyte having a mean crystal size of not more than 60 μm over the layer of a water-insoluble salt.

8. The process for the preparation of an integral ion selective electrode as claimed in claim 7, wherein said stage of drying the coated layer is performed by bringing it in contact with a stream of gas maintained at a temperature of not lower than 40° C.

9. The process for the preparation of an integral ion selective electrode as claimed in claim 7, wherein said mixture of water and an organic solvent is in the range of 2:8 to 8:2.

10. The process for the preparation of an integral ion selective electrode as claimed in any one of claims 7 to 9, wherein said organic solvent is selected from the group consisting of a lower aliphatic alcohol, an aliphatic ketone, ether, and an ester of a lower aliphatic acid with a lower aliphatic alcohol.

* * * * *